(12) United States Patent
Tixier et al.

(10) Patent No.: US 9,540,604 B2
(45) Date of Patent: Jan. 10, 2017

(54) APPARATUS AND METHOD FOR MONITORING AUTOTROPH CULTIVATION

(75) Inventors: Sebastien Tixier, North Vancouver (CA); Adrian M. Fuxman, North Vancouver (CA)

(73) Assignee: Honeywell Limited, Mississauga (CA)

( * ) Notice: Subject to any disclaimer, the term of this patent is extended or adjusted under 35 U.S.C. 154(b) by 1241 days.

(21) Appl. No.: 13/194,676

(22) Filed: Jul. 29, 2011

(65) Prior Publication Data

US 2013/0030715 A1      Jan. 31, 2013

(51) Int. Cl.
| | |
|---|---|
| G01N 33/00 | (2006.01) |
| C12M 1/00 | (2006.01) |
| C12M 1/34 | (2006.01) |
| G01N 21/49 | (2006.01) |
| G01N 21/59 | (2006.01) |
| G01N 21/63 | (2006.01) |

(52) U.S. Cl.
CPC ............ C12M 21/02 (2013.01); C12M 41/32 (2013.01); C12M 41/36 (2013.01); G01N 21/49 (2013.01); G01N 21/5907 (2013.01); G01N 2021/635 (2013.01)

(58) Field of Classification Search
CPC ............ C12M 41/30–41/32; G01N 2021/635
USPC .......................................................... 702/21
See application file for complete search history.

(56) References Cited

U.S. PATENT DOCUMENTS

| | | | |
|---|---|---|---|
| 8,033,047 B2 * | 10/2011 | Rasmussen et al. ............. 47/1.4 |
| 8,862,277 B1 * | 10/2014 | Campbell ............ A01G 25/167 |
| | | | 324/664 |
| 2009/0126265 A1 | 5/2009 | Rasmussen et al. |
| 2011/0020913 A1 * | 1/2011 | Rispoli et al. ............. 435/257.1 |
| 2011/0136212 A1 | 6/2011 | Parsheh et al. |

(Continued)

FOREIGN PATENT DOCUMENTS

| | | |
|---|---|---|
| WO | WO 03/023379 A1 | 3/2003 |
| WO | WO 2008/144583 A1 | 11/2008 |

(Continued)

OTHER PUBLICATIONS

Garrido et al., "Assessing chemical compounds for controlling predator ciliates in outdoor mass cultures of the green algae *Dunaliella salina*", 2001, Elsevier, Aquacultural Engineering 24, pp. 107-114.*

(Continued)

*Primary Examiner* — Sujoy Kundu
*Assistant Examiner* — Ricky Ngon (57) ABSTRACT

A method includes identifying a chlorophyll concentration/optical density (CCpOD) value using a chlorophyll concentration measurement of an autotroph culture and an optical density measurement of the autotroph culture. The method also includes identifying a change in the autotroph culture using the CCpOD value. The change in the autotroph culture can be identified by determining whether the CCpOD value falls outside upper and lower control limits. The upper and lower control limits can be identified using a specified number of previously-determined CCpOD values, which can be calculated when the autotroph culture is in a known healthy state. Multiple CCpOD values can be calculated, and an alarm can be generated if a specified number of the CCpOD values (such as one or more) fall outside the upper and lower control limits.

22 Claims, 4 Drawing Sheets

(56) References Cited

U.S. PATENT DOCUMENTS

| | | | |
|---|---|---|---|
| 2011/0273705 A1* | 11/2011 | Rao et al. | 356/222 |
| 2012/0073021 A1* | 3/2012 | Yuan | A01G 33/00 |
| | | | 800/296 |
| 2012/0309081 A1* | 12/2012 | Herzog | 435/288.7 |

FOREIGN PATENT DOCUMENTS

| | | | |
|---|---|---|---|
| WO | WO 2009108223 A2 * | 9/2009 | |
| WO | WO 2011/097261 A1 | 8/2011 | |
| WO | WO 2012/092666 A1 | 7/2012 | |

OTHER PUBLICATIONS

Notification of Transmittal of the International Search Report and the Written Opinion of the International Searching Authority, or the Declaration dated Aug. 27, 2012 in connection with International Patent Application No. PCT/CA2012/000467.

"The AlgaeTorch", bbe moldaenke, www.bbe-moldaenke.de, 2 pages.

"The NEW bbe AlgaeTorch", bbe moldaenke, www.bbe-moldaenke.de, Nov. 2008, 1 page.

"Turbidity Measurement at no extra cost!", bbe moldaenke, www.bbe-moldaenke.de, Aug. 2010, 2 pages.

Susan Award, et al., "Effect of Cadmium on the growth of Chlamydomonas", The Journal of Young Investigators: An Undergraduate, Peer-Reviewed Science Journal, vol. 13, Issue 3, Aug. 31, 2005, 9 pages.

M. Beutler, et al., "A fluorometric method for the differentiation of algal populations in vivo and in situ", Photosynthesis Research, vol. 72, 2002, p. 39-53.

"FluoroProbe, Submersible Spectrofluorometer with Automatic Algae Class and Chlorophyll Analysis", bbe moldaenke, www.bbe-moldaenke.de, 4 pages.

"The new FluoroProbe III", bbe moldaenke, www.bbe-moldaenke.de, 2008, 1 page.

"Fluorometer and Scattering Meter", WET Labs eco flntu; WET Labs, Inc., www.wetlabs.com Sep. 21, 2010, 1 page.

Notification of Transmittal of the International Search Report and the Written Opinion of the International Searching Authority, or the Declaration dated Apr. 10, 2012 in connection with International Patent Application No. PCT/CA2012/000005.

European Examination Report dated Jun. 25, 2015 in connection with European Patent Application No. 12820107.6; 8 pages.

Marxen, et al.; "A photobioreactor system for computer controlled cultivation of microalgae"; Journal of Applied Phycology; 2005; pp. 535-549.

Schottkowski, et al.; "Pitt, a Novel Tetratricopeptide Repeat Protein Involved in Light-Dependent Cholorophyll Biosynthesis and Thylakoid Membrane Biogenesis in Synechocystis sp. PCC 6803" Molecular Plant; vol. 2, No. 6; Nov. 2009; pp. 1289-1297.

Office Action issued for European Application No. 12820107.6 dated Jan. 21, 2016, 5 pgs.

* cited by examiner

APPARATUS AND METHOD FOR MONITORING AUTOTROPH CULTIVATION

TECHNICAL FIELD

This disclosure relates generally to process monitoring systems. More specifically, this disclosure relates to an apparatus and method for monitoring autotroph cultivation.

BACKGROUND

Algae generally includes a large and diverse group of simple, typically autotrophic organisms that grow using photosynthesis. Photosynthesis is a process where plants generate higher-order organic compounds, such as sugars, using a chemical process involving chlorophyll. Chlorophyll is generally characterized by a green pigment found in most living plants.

Because some species of algae grow at a relatively fast rate, their use has been explored in the cultivation of food and energy. Algae of this type has been cultivated in open ponds and in closed reactors in which the algae is suspended in a water solution and periodically provided with nutrients for its growth. Algae cultivation may be performed for various purposes, including industrial and municipal waste water remediation, growing high value food supplements (such as spirulina), growing food for aquaculture, and biofuel cultivation from algal lipids.

SUMMARY

This disclosure provides an apparatus and method for monitoring autotroph cultivation.

In a first embodiment, an apparatus includes at least one processing unit configured to determine a chlorophyll concentration per optical density (CCpOD) value using a chlorophyll concentration measurement of an autotroph culture and an optical density measurement of the autotroph culture. The at least one processing unit is also configured to identify a change in the autotroph culture using the CCpOD value.

In a second embodiment, a method includes identifying a CCpOD value using a chlorophyll concentration measurement of an autotroph culture and an optical density measurement of the autotroph culture. The method also includes identifying a change in the autotroph culture using the CCpOD value.

In a third embodiment, a system includes a first measuring device configured to measure a chlorophyll concentration of an autotroph culture and a second measuring device configured to measure an optical density of the autotroph culture. The system further includes a monitoring device configured to receive a chlorophyll concentration measurement from the first measuring device and receive an optical density measurement from the second measuring device. The monitoring device is also configured to identify a CCpOD value using the chlorophyll concentration measurement and the optical density measurement and identify a change in the autotroph culture using the CCpOD value.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device(s) or system(s).

Figure 1:
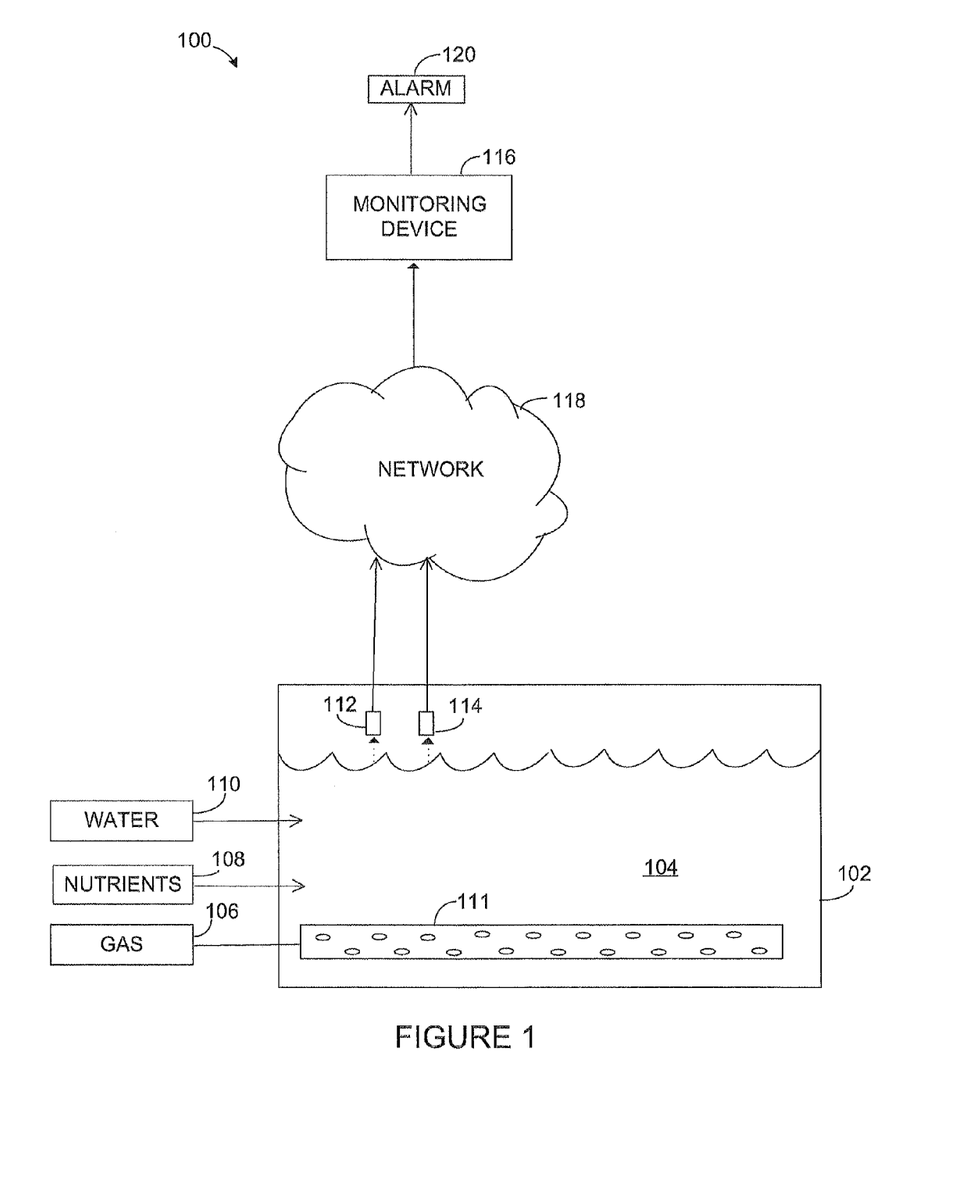
FIG. 1 illustrates an example system for monitoring autotroph cultivation according to this disclosure.

FIG. 1 illustrates an example system 100 for monitoring autotroph cultivation according to this disclosure. In the following description, reference is made to monitoring the cultivation of algae. However, the system 100 could be used to monitor any autotroph cultivation. Autotrophs include organisms that receive their energy from light (such as photoautotrophs like microalgae, macroalgae, phytoplankton, and cyanobacteria) or inorganic chemical reactions (like chemoautotrophs).

As described above, the relatively fast growth rate of certain algae species makes those species useful in a number of applications like waste water remediation, food supplementation, and biofuel cultivation. A challenge in large-scale algae cultivation is maintaining algae cultivation at an optimal level. Various factors may affect the cultivation rate of certain algae cultures. For example, the coexistence of various algae species may change over time due to, for instance, a commensurate change in environmental conditions like weather, and lead to changes in the predominant algae species. As another example, the cultivation rate of algae cultures may change due to coexistence with other microorganisms, such as bacteria, mold, and other grazers or predators. Grazers refer to microorganisms that steal or otherwise consume nutrients intended for an algae culture, while predators refer to microorganisms that consume the algae culture.

Conventional systems often use chlorophyll concentration measuring devices and/or turbidity measuring devices independently of one another to monitor an algae culture. However, even a healthy algae culture may grow at varying rates due to various factors, such as seasonal changes, sunlight, temperature, and availability of nutrients. Thus, changes in chlorophyll concentration levels would be expected as an algae culture grows, particularly in water-suspended cultures where the algae itself may exist at differing concentration levels in a suspended solution of water. Because chlorophyll concentration by itself may normally change in a healthy algae culture, distinguishing between normal changes and harmful changes in the algae culture is often difficult to assess when using only conventional techniques and methods.

In accordance with this disclosure, an autotroph monitoring system measures a chlorophyll concentration per optical density (CCpOD) parameter. The use of this parameter can provide enhanced detection of changes that may be difficult to observe when only chlorophyll concentrations are measured. Thus, by monitoring an autotroph culture using CCpOD values, enhanced detection of harmful changes in the autotroph culture can be achieved. These harmful changes can include changes in speciation and increased grazer or predator levels.

As shown in FIG. 1, the system 100 includes a tank 102 in which an autotroph culture 104 is held. The system 100 also includes components that supply certain items to the autotroph culture 104. In this particular example, an gas supply 106 provides one or more gasses (such as carbon dioxide and/or atmospheric air) to the autotroph culture 104. Also, a nutrient supply 108 provides nutrients for the autotroph culture's growth. A water supply 110 provides fresh water to the autotroph culture 104. The air from the air supply 106 may be supplied to the tank 102 via a diffuser 111, which diffuses the air into the liquid in the tank 102. Any other or additional equipment or components could be used in the system 100.

The system 100 also includes a chlorophyll concentration measuring device 112 that measures the chlorophyll concentration of the autotroph culture 104. The system 100 further includes an optical density measuring device 114 that measures an optical density of the autotroph culture 104. The measuring devices 112-114 provide their respective measurements to a monitoring device 116, such as via a network 118 or through a direct connection. The chlorophyll concentration measuring device 112 includes any suitable structure for measuring chlorophyll concentration. The optical density measuring device 114 includes any suitable structure for measuring optical density.

The monitoring device 116 receives measurements from the measuring devices 112-114, such as at a periodic interval or at any other suitable times. The monitoring device 116 also determines a chlorophyll concentration per optical density (CCpOD) parameter value based on those measurements. In one embodiment, the CCpOD value can be calculated as $(Cst_1*\text{Chorophyll concentration})-Cst_2*\text{turbidity})-Cst_3$ where the constants $Cst_1$, $Cst_2$, and $Cst_3$ are obtained by calibrating the chlorophyll sensor and the turbidity sensor to a dry biomass (or by calibrating one sensor to the other) using samples of a healthy culture. In another embodiment, the CCpOD value can be calculated as $(Cst_1*\text{chlorophyll concentration})-(\text{turbidity}+Cst_2)$. This particular calculation of CCpOD may be used in cases where the chlorophyll sensor is calibrated to turbidity and a generally healthy culture is assumed in which chlorophyll and turbidity values are linearly correlated.

In other embodiments, however, the chlorophyll and turbidity values are not necessarily linearly correlated and more complex functions for relating the chlorophyll concentration to turbidity may be used. The calculated CCpOD values could then be used in any suitable manner. For example, in some embodiments, the monitoring device 116 may continually monitor the autotroph culture 104 by periodically determining the CCpOD value and generating an alarm 120 if the CCpOD value exceeds a threshold for a specified period of time (such as a single CCpOD value or a number of CCpOD values). The monitoring device 116 could also output the CCpOD values to another component that compares the CCpOD values to the threshold.

The chlorophyll concentration measuring device 112 uses any suitable technique to measure chlorophyll concentrations of an autotroph culture 104. In some embodiments, the measuring device 112 uses extractive analysis to measure chlorophyll concentration of the autotroph culture. In the extractive analysis technique, a sample is taken from the autotroph culture, and the cells of the culture are collected by centrifugation or membrane filtration. The pigments are then extracted using one or more solvents, such as acetone, methanol, or diethyl-ether. The extract is measured using light absorption or fluorescence techniques.

In some embodiments of the fluorescence technique, a blue light is directed toward the extract to excite the chlorophyll molecules. This causes the chlorophyll molecules to fluoresce or emit light, such as at a relatively longer wavelength typically in the red light region of about 650 nm to 700 nm. In a particular example, the blue excitation light has a wavelength of about 470 nm, although any suitable wavelength may be used that causes the chlorophyll molecules to fluoresce and emit light that can be measured. The chlorophyll concentration may be determined by measuring the level of light fluoresced from the sample.

In some embodiments of the direct measurement technique, the fluorescence technique may be applied in-situ. That is, the direct measurement technique may measure chlorophyll concentration levels directly without removal of a sample from the autotroph culture. The direct measurement technique could be used, for example, for on-line sensing when the autotroph culture 104 is in a remote or difficult to access location. In some cases, a measuring device 112 utilizing the direct measurement technique may be calibrated at periodic intervals to provide relatively good accuracy.

The optical density measuring device 114 also uses any suitable technique for measuring the optical density of the autotroph culture 104. The optical density of the autotroph culture is a product all species present in the culture 104, which may include various forms of organic and inorganic matter.

In some embodiments, the measuring device 114 uses a total suspended solids (TSS) measurement in place of the optical density measurement, which is typically performed in a laboratory environment. A TSS measurement typically involves separating solids from an aqueous medium, washing and drying the separated solids, and weighing the resulting solids to determine a level of TSS of the autotroph culture. In particular embodiments, this procedure may be automated by the measuring device 114 so that optical density measurements may be obtained on-line without manual intervention.

In other embodiments, the measuring device 114 uses a light scattering technique. In this technique, a column of light is directed into a sample of the autotroph culture 104, and reflected or scattered light from the light column is measured at one or more angles relative to the incident light column. In some respects, the light scattering technique may also refer to turbidity or TSS measurements of an aqueous medium. The light source may have any suitable wavelength, such as a red or infrared light source having a wavelength of approximately 700 nm. The light scattering technique may be well suited for in-situ measurements of the autotroph culture 104. Relatively good accuracy may be obtained using periodic calibration over an extended period of time while monitoring of the autotroph culture 104.

As noted above, chlorophyll concentration and optical density measurements may be communicated to the monitoring device 116 directly or over a network 118. The use of the network 118 could, for example, facilitate the monitoring of autotroph cultures at remote locations where access may be relatively difficult. Also, the monitoring device 116 may be configured to monitor the CCpOD parameters of multiple autotroph cultures at a single centralized location. The network 118 represents any suitable network or combination of networks, such as an Ethernet network, an electrical signal network (like a HART or FOUNDATION FIELDBUS network), or any other or additional type(s) of network(s).

Figure 2:
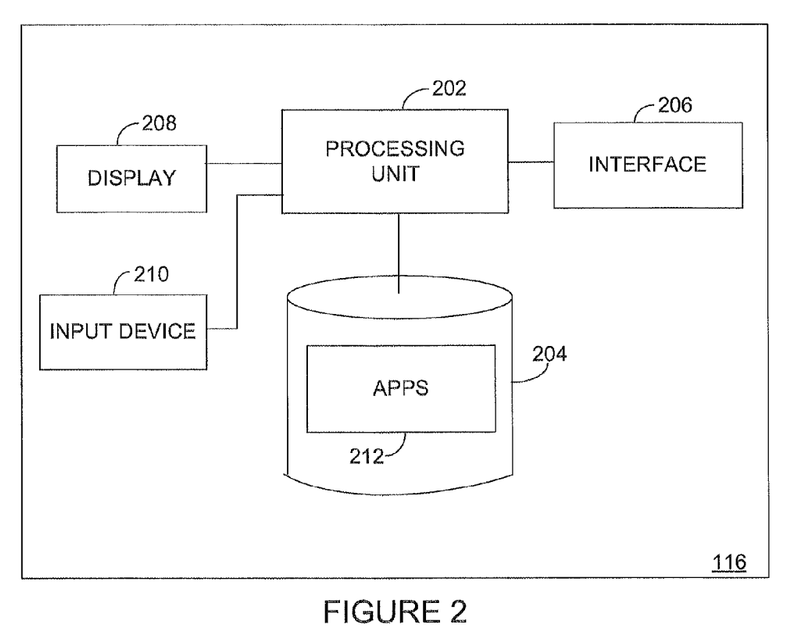
FIG. 2 illustrates an example monitoring device for monitoring autotroph cultivation according to this disclosure.

The monitoring device 116 includes any suitable structure for monitoring one or more autotroph cultures 104. The monitoring device 116 could, for example, be implemented using hardware or a combination of hardware and software/firmware instructions. An example embodiment of the monitoring device 116 is shown in FIG. 2, which is described below. In particular embodiments, the monitoring device 116 could include an EXPERION OPC server, an EXPERION HS server, an EXPERION server pair, or an EXPERION EAS server from HONEYWELL INTERNATIONAL INC.

Although FIG. 1 illustrates one example of a system 100 for monitoring autotroph cultivation, various changes may be made to FIG. 1. For example, the autotroph culture 104 could be contained in any other suitable structure, such as a man-made reservoir, an enclosed hermetic tank, or an open structure. As another example, the functional division shown in FIG. 1 is for illustration only. Various components in FIG. 1 could be omitted, combined, or further subdivided and additional components could be added according to particular needs. As specific examples, the measuring devices 112-114 could be combined into a single unit, the monitoring device 116 could be incorporated into one of the measuring devices 112-114, or all three components 112-116 could be combined into a single functional unit. In addition, the functionality of the monitoring device 116 could be used in any other suitable device or system.

FIG. 2 illustrates an example monitoring device 116 for monitoring autotroph cultivation according to this disclosure. As shown in FIG. 2, the monitoring device 116 includes at least one processing unit 202, at least one memory unit 204, at least one interface 206, a display 208, and at least one input device 210.

The processing unit 202 represents any suitable processing device(s), such as a microprocessor, microcontroller, digital signal processor, application-specific integrated circuit, field programmable gate array, or other logic device. The memory unit 204 represents any suitable volatile and/or non-volatile storage and retrieval device(s), such as random access or read-only memory. The interface 206 represents any suitable interface for facilitating communication over one or more networks, such as an Ethernet interface or other electrical signal line interface or a wireless interface. The interface 206 can be used to receive chlorophyll concentration and optical density measurements or to output data to other devices or system. The display 208 represents any suitable display device for presenting information to a user. The input device 210 represents any suitable device(s) for receiving input from a user, such as a keyboard or mouse.

In FIG. 2, the memory unit 204 includes at least one application 212. The application 212 represents one or more computer programs defining how the monitoring device 116 monitors an autotroph culture 104. For example, the application 212 may include instructions for calculating the CCpOD parameter values and an analysis tool that processes the CCpOD values using statistical process modeling techniques. For example, the application 212 may generate histograms of past CCpOD measurements to determine upper and lower process control points (commonly referred to as standard deviation values). The analysis could be done at a regular on-going interval. The application 212 could also include instructions for generating the alarm 120 if one or more CCpOD measurements exceed either of the standard deviation values established using the histogram distributions.

Although FIG. 2 illustrates one example of a monitoring device 116 for monitoring autotroph cultivation, various changes may be made to FIG. 2. For example, the monitoring device 116 could include any other or additional components according to particular needs. Also, the monitoring device 116 could be implemented using any suitable monitoring or control technology. In addition, the monitoring device 116 could be used to monitor and/or control one or multiple autotroph cultures.

Figure 3A:
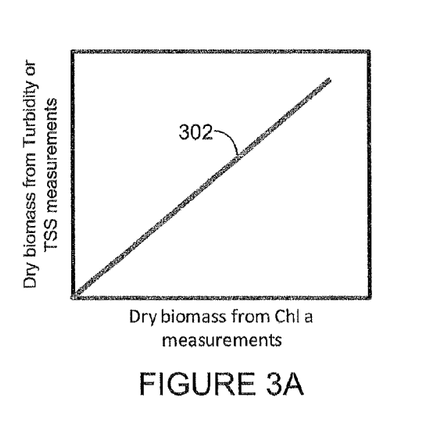
FIGS. 3A and 3B illustrate example chlorophyll concentration per optical density (CCpOD) measurements for autotroph cultures according to this disclosure.
Figure 3B:
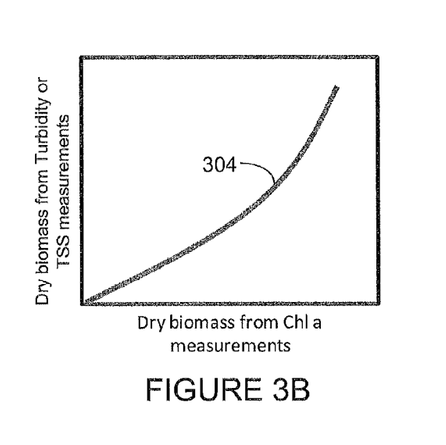

FIGS. 3A and 3B illustrate example CCpOD measurements for autotroph cultures according to this disclosure. Specifically, FIG. 3A illustrates CCpOD measurements 302 for an autotroph culture in which no change takes place (except for desired growth), while FIG. 3B illustrates CCpOD measurements 304 exhibiting a changed algae culture.

As shown in FIG. 3A, the CCpOD measurements 302 are relatively linear because the dry biomass as calculated from the optical density (ie. turbidity) sensor is equal to the dry biomass as calculated from the chlorophyll sensor. This may occur, for example, in a newly started algae culture, which may exhibit a relatively low chlorophyll concentration because the aqueous medium has been recently seeded with algae. In this case, the algae culture would exhibit a relatively low optical density. As the culture continues to mature, the optical density level would increase commensurate with an increase in algae growth. This example represents a desired healthy case in which algae growth occurs normally.

In some embodiments, the CCpOD measurements shown in FIG. 3A may be based on a calibration performed when the culture exists in a known healthy state (such as early in the life of the culture). Later during the life of the culture, subsequent measurements may be obtained and compared with the calibration to determine if the culture is suffering from some abnormality. Note that different species of algae may exhibit different CCpOD values relative to one another. Conversely, similar species may exhibit relatively similar CCpOD values in spite of being measured from different cultures or at different times. As a result, a CCpOD calibration may be generated for a known healthy culture during one particular growing season. If the same species is grown in the next growing season (such as a year later) with relatively similar environmental conditions, the CCpOD calibration from the previous growing season could be used to monitor the algae culture in the next growing season.

As shown in FIG. 3B, the chlorophyll culture does not evolve as the case of the healthy culture as shown in FIG. 3A. The dry biomass as calculated from turbidity is not proportional to the dry biomass as calculated from the chlorophyll concentration. The culture has changed state compared to the healthy state, that is, the turbidity to dry biomass and chlorophyll concentration to dry biomass calibration time. In some cases, this may indicate that the culture has become unhealthy. In other cases, this may merely indicate that some change has occurred. For example, the culture may be originally seeded with a certain sub-genus of algal organisms encompassing multiple species of algae. Due to a change of environmental conditions, one or more of these species may begin to dominate the culture, and the resulting CCpOD measurements change even though the culture has remained relatively healthy. Although this may not indicate an unhealthy condition, personnel may use the CCpOD measurements to detect changes in the culture so that the culture may be adequately controlled.

Although FIGS. 3A and 3B illustrate examples of CCpOD measurements for autotroph cultures, various changes may be made to FIGS. 3A and 3B. For example, FIGS. 3A and 3B merely show example CCpOD measurements that could be determined for specific autotroph cultures. Since the content and makeup of autotroph cultures may vary widely, other autotroph cultures may exhibit differing CCpOD functions relative to those shown in FIGS. 3A and 3B.

Figure 4:
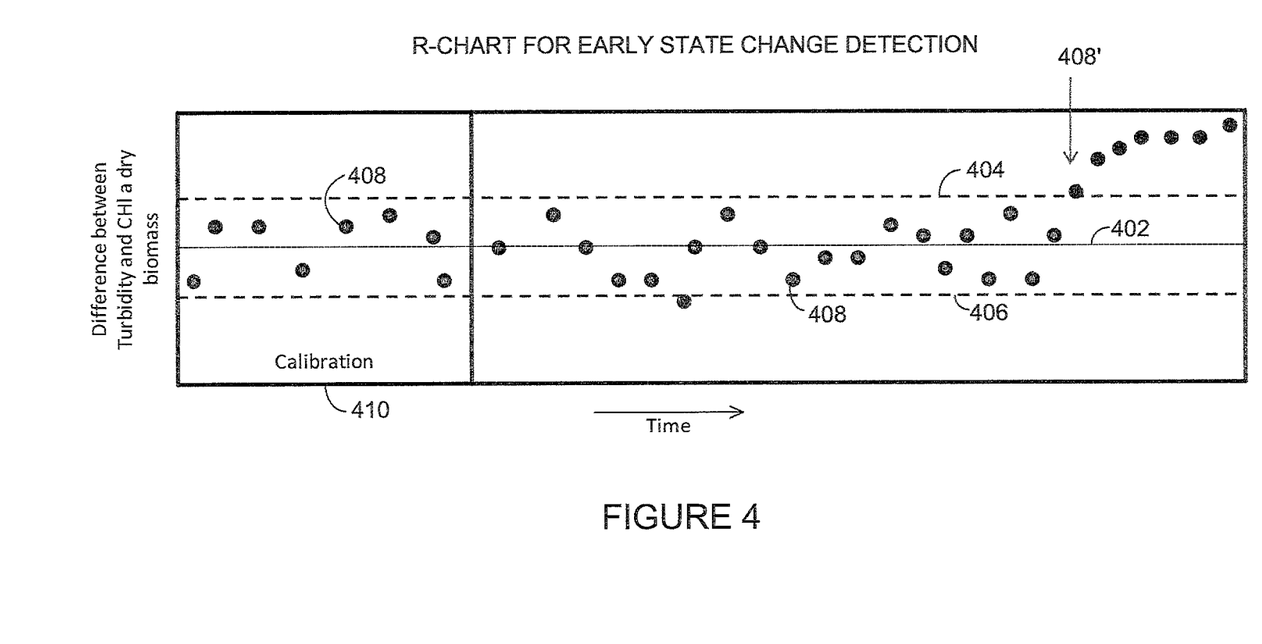
FIG. 4 illustrates an example control chart for an autotroph culture according to this disclosure.

FIG. 4 illustrates an example control chart 400 for an autotroph culture according to this disclosure. The control chart 400 could, for example, be generated by the monitoring device 116 of FIG. 1.

In this example, the control chart 400 represents a process variation chart (R-chart) includes a median line 402, an upper control limit line 404, a lower control limit line 406, and CCpOD parameter values 408 plotted over time. The median line 402 shows the mean value of a specified number of previously-received CCpOD values 408. The control limit lines 404-406 show the upper and lower process control points (standard deviation values), which can be determined using any suitable statistical modeling process. In some embodiments, the control limit lines 404-406 can be calculated using a specified number of CCpOD values 408 determined during a calibration stage 410.

In some embodiments, the CCpOD values 404 are received and processed at a specified interval, such as a one-hour interval. Any suitable interval could be used, such as one that provides sufficient granularity to detect a change in an autotroph culture so that proper remedial action may be taken to maintain the culture in a relatively consistent state. Also, in this example, the control limit lines 404-406 are set at a 3-sigma point of the standard deviation of previously-acquired CCpOD values 408. However, the control limit lines 404-406 may be set to any other suitable value(s).

Also shown in FIG. 4 are CCpOD parameter values 408' that have exceeded the upper control limit line 404. This indicates that chlorophyll derived dry biomass minus turbidity derived dry biomass instead of difference between turbidity and Chlorophyll dry biomass. In cases such as this, the monitoring device 116 may generate an alarm 120 to alert personnel of the change in the culture.

Although FIG. 4 illustrates one example of a control chart 400 for an autotroph culture, various changes may be made to FIG. 4. For example, any other type of control chart could be used. As a particular example, the control chart may include a bar-X chart and/or an S-chart that shows a statistical progression of the CCpOD parameter value in an autotroph culture.

Figure 5:
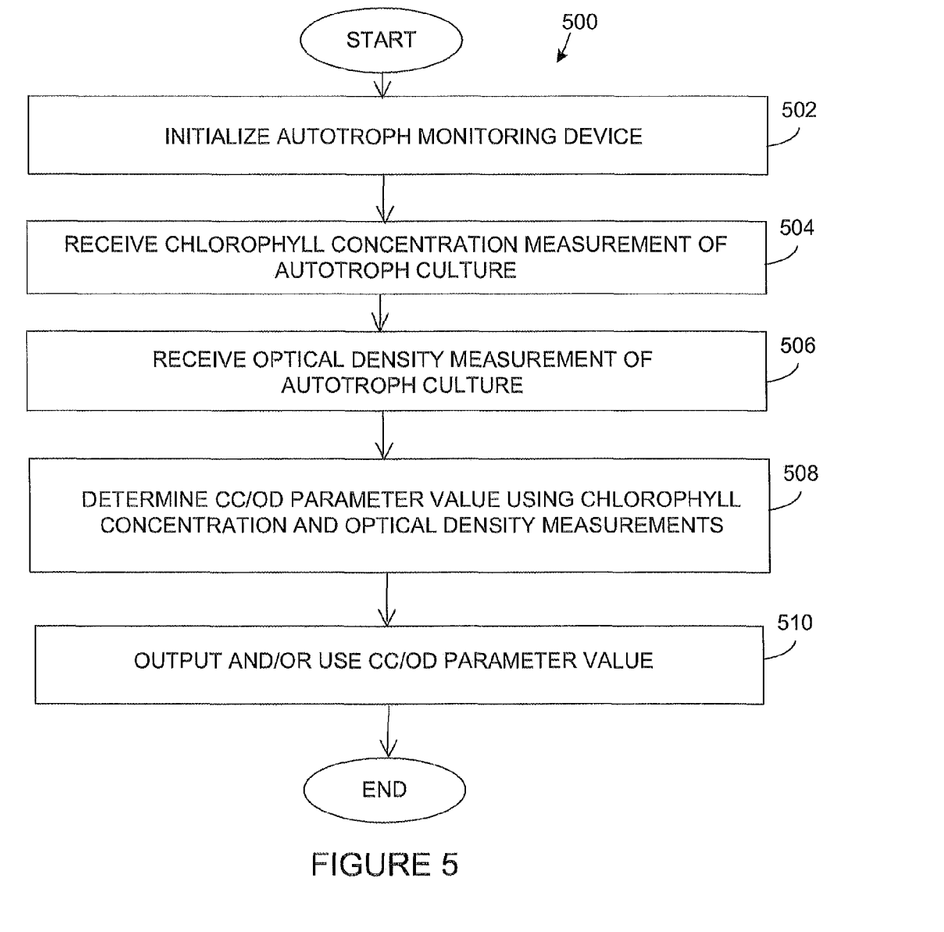
FIG. 5 illustrates an example method for monitoring autotroph cultivation according to this disclosure.

FIG. 5 illustrates an example method 500 for monitoring autotroph cultivation according to this disclosure. As shown in FIG. 5, an autotroph monitoring device is initialized at step 502. This could include, for example, setting certain device settings during the calibration stage 410 of the monitoring device 116.

A chlorophyll concentration measurement for an autotroph culture is received at step 504, and an optical density measurement for the autotroph culture is received at step 506. The chlorophyll concentration measurement may be determined using any suitable technique, such as an extractive analysis or direct measurement technique. Also, the optical density measurement may be determined using any suitable technique, such as a light scattering technique.

The monitoring device determines a CCpOD parameter value for the autotroph culture at step 508. The CCpOD parameter may be calculated as described above with reference to FIG. 1. The CCpOD parameter value is then output and/or used in some manner at step 510. For example, the latest CCpOD parameter value may be compared with a previously-calculated CCpOD parameter value to determine it any change has occurred in the autotroph culture 104. If a significant change is detected, the monitoring device 116 could generate an alarm 120 or take some other action, such as automatically adjusting the components 106-110 providing materials to the culture 104.

Although FIG. 5 illustrates one example of a method 500 for monitoring autotroph cultivation, various changes may be made to FIG. 5. For example, while shown as a series of steps, various steps in FIG. 5 could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "include" and "comprise," as well as derivatives thereof, mean inclusion without limitation. The term "or" is inclusive, meaning and/or. The phrase "associated with" and its derivatives mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "receive" and its derivatives include receipt from an external source or an internal source.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   at least one processing device configured to:
      receive a chlorophyll concentration measurement of an autotroph culture from a chlorophyll sensor;
      receive an optical density measurement of the autotroph culture from an optical density sensor;
      determine a chlorophyll concentration per optical density (CCpOD) value that is a function of the chlorophyll concentration measurement of the autotroph culture and the optical density measurement of the autotroph culture;
      identify a change in the autotroph culture using the CCpOD value;

detect a contamination of the autotroph culture based on the identified change in the autotroph culture, the contamination including a presence of grazers or predators in the autotroph culture, the grazers comprising microorganisms that consume nutrients intended for the autotroph culture, the predators comprising microorganisms that consume the autotroph culture; and generate control signals to adjust at least one characteristic associated with the autotroph culture based on the identified change in the autotroph culture by automatically adjusting a supply component configured to provide at least one of gas, liquid, or nutrients to the autotroph culture.

2. The apparatus of claim 1, wherein the at least one processing device is further configured to:
calculate multiple CCpOD values; and
generate an alarm if a specified number of the CCpOD values fall outside a range defined by upper and lower control limits.

3. The apparatus of claim 2, wherein the at least one processing device is further configured to identify the upper and lower control limits using a specified number of previously-calculated CCpOD values.

4. The apparatus of claim 3, wherein the previously-calculated CCpOD values are calculated when the autotroph culture is in a known healthy state.

5. The apparatus of claim 1, further comprising:
at least one interface configured to receive the chlorophyll concentration measurement from the chlorophyll sensor and the optical density measurement from the optical density sensor.

6. The apparatus of claim 1, further comprising:
the chlorophyll sensor configured to generate the chlorophyll concentration measurement.

7. The apparatus of claim 1, further comprising:
the optical density sensor configured to generate the optical density measurement.

8. The apparatus of claim 1, further comprising:
at least one memory device configured to store the CCpOD value and previously-calculated CCpOD values.

9. The apparatus of claim 1, wherein the autotroph culture comprises algae.

10. The apparatus of claim 1, wherein the change is a changed state of the culture compared to a known healthy state.

11. The apparatus of claim 1, wherein the at least one processing device is configured to calculate the CCpOD value using multiple constants obtained by calibrating the chlorophyll sensor and a turbidity sensor to dry biomass using samples of a healthy autotroph culture.

12. A method comprising:
identifying, by a monitoring device, a calculated chlorophyll concentration per optical density (CCpOD) value that is calculated as a function of a chlorophyll concentration measurement of an autotroph culture and an optical density measurement of the autotroph culture;
identifying a change in the autotroph culture using the CCpOD value;
detecting a contamination of the autotroph culture based on the identified change in the autotroph culture, the contamination including a presence of grazers or predators in the autotroph culture, the grazers comprising microorganisms that consume nutrients intended for the autotroph culture, the predators comprising microorganisms that consume the autotroph culture; and adjusting at least one characteristic associated with the autotroph culture based on the identified change in the autotroph culture by automatically adjusting a supply component configured to provide at least one of gas, liquid, or nutrients to the autotroph culture.

13. The method of claim 12, wherein identifying the CCpOD value comprises:
receiving the chlorophyll concentration measurement from a chlorophyll sensor; and
receiving the optical density measurement from an optical density sensor.

14. The method of claim 12, further comprising:
calculating multiple CCpOD values; and
generating an alarm if a specified number of the CCpOD values fall outside a range defined by upper and lower control limits.

15. The method of claim 12, wherein the change is a changed state of the culture compared to a known healthy state.

16. A system comprising:
a chlorophyll sensor configured to measure a chlorophyll concentration of an autotroph culture;
an optical density sensor configured to measure an optical density of the autotroph culture; and
a monitoring device configured to:
receive a chlorophyll concentration measurement from the chlorophyll sensor;
receive an optical density measurement from the optical density sensor;
determine a chlorophyll concentration per optical density (CCpOD) value that is a function of the chlorophyll concentration measurement and the optical density measurement;
identify a change in the autotroph culture using the CCpOD value;
detect a contamination of the autotroph culture based on the identified change in the autotroph culture, the contamination including a presence of grazers or predators in the autotroph culture, the grazers comprising microorganisms that consume nutrients intended for the autotroph culture, the predators comprising microorganisms that consume the autotroph culture; and
generate control signals to adjust at least one characteristic associated with the autotroph culture based on the identified change in the autotroph culture by automatically adjusting a supply component configured to provide at least one of gas, liquid, or nutrients to the autotroph culture.

17. The system of claim 16, wherein the monitoring device is further configured to:
identify upper and lower control limits using a specified number of previously-calculated CCpOD values; and
determine whether the CCpOD value falls outside a range defined by the upper and lower control limits.

18. The system of claim 16, wherein the monitoring device is further configured to:
calculate multiple CCpOD values; and
generate an alarm if a specified number of the CCpOD values fall outside a range defined by upper and lower control limits.

19. An apparatus comprising:
at least one processing device configured to:
receive a chlorophyll concentration measurement of an autotroph culture from a chlorophyll sensor;
receive an optical density measurement of the autotroph culture from an optical density sensor;

calculate a chlorophyll concentration per optical density (CCpOD) value that is a function of the chlorophyll concentration measurement of the autotroph culture and the optical density measurement of the autotroph culture;

identify a change in the autotroph culture using the CCpOD value by determining whether the CCpOD value falls outside a range defined by upper and lower control limits; and when the change is identified, automatically adjust a supply component configured to provide at least one of gas, liquid, or nutrients to the autotroph culture;

wherein the at least one processing device is configured to calculate the CCpOD value according to:

$$(Cst_1 * \text{chlorophyll concentration measurement} - Cst_2 * \text{turbidity}) - Cst_3$$

wherein $Cst_1$, $Cst_2$, and $Cst_3$ are constants obtained by calibrating the chlorophyll sensor and a turbidity sensor to dry biomass using samples of a healthy autotroph culture, the healthy autotroph culture having linearly-correlated chlorophyll and turbidity values;

wherein turbidity is a measure of total biomass including algal and non-algal biomass that is measured by the turbidity sensor; and wherein the at least one processing device is configured to receive the turbidity from the turbidity sensor.

20. The apparatus of claim 19, wherein the at least one processing device is further configured to identify the upper and lower control limits using a specified number of previously-calculated CCpOD values.

21. An apparatus comprising:
at least one processing device configured to:
receive a chlorophyll concentration measurement of an autotroph culture from a chlorophyll sensor;

receive an optical density measurement of the autotroph culture from an optical density sensor;

calculate a chlorophyll concentration per optical density (CCpOD) value that is a function of the chlorophyll concentration measurement of the autotroph culture and the optical density measurement of the autotroph culture;

identify a change in the autotroph culture using the CCpOD value by determining whether the CCpOD value falls outside a range defined by upper and lower control limits; and when the change is identified, automatically adjust a supply component configured to provide at least one of gas, liquid, or nutrients to the autotroph culture;

wherein the at least one processing device is configured to calculate the CCpOD value according to:

$$(Cst_1 * \text{chlorophyll concentration measurement}) - \text{turbidity} - Cst_2$$

wherein $Cst_1$ and $Cst_2$ are constants obtained by calibrating the chlorophyll sensor and a turbidity sensor to dry biomass using samples of a healthy autotroph culture, the healthy autotroph culture having linearly-correlated chlorophyll and turbidity values;

wherein turbidity is a measure of total biomass including algal and non-algal biomass that is measured by the turbidity sensor; and wherein the at least one processing device is configured to receive the turbidity from the turbidity sensor.

22. The apparatus of claim 21, wherein the upper and lower control limits are based on predetermined CCpOD values.

* * * * *